(12) United States Patent
Dubey et al.

(10) Patent No.: US 12,290,690 B2
(45) Date of Patent: May 6, 2025

(54) BIOSTIMULATOR HAVING PATCH ANTENNA

(71) Applicant: PACESETTER, INC, Sylmar, CA (US)

(72) Inventors: Souvik Dubey, Woodland Hills, CA (US); Perry Li, Arcadia, CA (US); Craig E. Mar, Fremont, CA (US)

(73) Assignee: PACESETTER, INC., Sylmar, CA (US)

( * ) Notice: Subject to any disclaimer, the term of this patent is extended or adjusted under 35 U.S.C. 154(b) by 116 days.

(21) Appl. No.: 17/182,092

(22) Filed: Feb. 22, 2021

(65) Prior Publication Data

US 2021/0260389 A1    Aug. 26, 2021

Related U.S. Application Data

(60) Provisional application No. 62/981,301, filed on Feb. 25, 2020.

(51) Int. Cl.
*A61N 1/372* (2006.01)
*A61N 1/05* (2006.01)
(Continued)

(52) U.S. Cl.
CPC ....... *A61N 1/37229* (2013.01); *A61N 1/0573* (2013.01); *A61N 1/37512* (2017.08);
(Continued)

(58) Field of Classification Search
CPC .............. A61N 1/37229; A61N 1/0573; A61N 1/37512; A61N 1/3754; A61N 1/3756
(Continued)

(56) References Cited

U.S. PATENT DOCUMENTS 5,450,090 A * 9/1995 Gels ...................... H01Q 9/0414
343/846
6,731,245 B1 * 5/2004 Stotler ................. H01Q 9/0435
343/702
(Continued)

FOREIGN PATENT DOCUMENTS

EP    1362614 B1    3/2008
EP    2579387 B1    7/2014
(Continued)

*Primary Examiner* — Joseph M Dietrich
*Assistant Examiner* — Michael T. Holtzclaw
(74) *Attorney, Agent, or Firm* — WOMBLE BOND DICKINSON (US) LLP

(57) ABSTRACT

A biostimulator, such as a leadless cardiac pacemaker, having a patch antenna integrated into a housing, is described. The housing includes an annular wall that contains electronic circuitry of the biostimulator and provides a ground plane of the antenna. The patch antenna includes a meandering trace embedded in a curved dielectric layer that is mounted on the annular wall. The trace provides a conductor of the antenna and the dielectric layer provides a dielectric substrate of the antenna between the conductor and the ground plane. The electronic circuitry contained within the annular wall is electrically connected to the trace via an electrical feedthrough that passes through the annular wall and the dielectric layer. The electrical feedthrough places the electronic circuitry in communication with the antenna to transmit or receive wireless communication signals from an external device. Other embodiments are also described and claimed.

20 Claims, 8 Drawing Sheets

(51) Int. Cl.
*A61N 1/375* (2006.01)
*H01Q 1/42* (2006.01)
*H01Q 9/04* (2006.01)

(52) U.S. Cl.
CPC ......... *A61N 1/3754* (2013.01); *A61N 1/3756* (2013.01); *H01Q 1/42* (2013.01); *H01Q 9/0407* (2013.01)

(58) Field of Classification Search
USPC .......................................................... 607/32
See application file for complete search history.

(56) References Cited

U.S. PATENT DOCUMENTS

| | | | |
|---|---|---|---|
| 7,072,718 B2 | 7/2006 | Von Arx et al. | |
| 8,514,136 B2 | 8/2013 | McCarthy et al. | |
| RE45,030 E | 7/2014 | Stevenson et al. | |
| 10,396,451 B2 | 8/2019 | Spencer et al. | |
| 2003/0216793 A1* | 11/2003 | Karlsson | H01Q 9/0421 607/60 |
| 2005/0134520 A1* | 6/2005 | Rawat | A61N 1/37229 343/873 |
| 2006/0284784 A1* | 12/2006 | Smith | G01D 4/008 343/872 |
| 2010/0019985 A1* | 1/2010 | Bashyam | A61N 1/37518 343/873 |
| 2010/0109966 A1* | 5/2010 | Mateychuk | H01Q 9/42 427/2.24 |
| 2010/0280568 A1* | 11/2010 | Bulkes | A61N 1/056 607/33 |
| 2012/0130451 A1* | 5/2012 | Vajha | H01Q 1/36 607/60 |
| 2016/0250471 A1* | 9/2016 | Khalil | A61N 1/37229 607/46 |
| 2017/0065207 A1* | 3/2017 | Landherr | A61B 5/0031 |
| 2018/0028821 A1 | 2/2018 | Starke et al. | |
| 2018/0131085 A1* | 5/2018 | Cappa | H01Q 1/22 |
| 2018/0280703 A1* | 10/2018 | Hillukka | A61N 1/3756 |
| 2019/0030346 A1 | 1/2019 | Li et al. | |
| 2019/0232066 A1* | 8/2019 | Lim | A61N 1/3754 |
| 2019/0299014 A1* | 10/2019 | Lim | A61N 1/37229 |
| 2020/0001095 A1* | 1/2020 | Iyer | A61N 1/37229 |
| 2020/0005988 A1* | 1/2020 | Iyer | A61N 1/3975 |
| 2020/0021017 A1 | 1/2020 | Kirknes | |

FOREIGN PATENT DOCUMENTS

| | | |
|---|---|---|
| GB | 2414408 A | 11/2005 |
| WO | 2000048266 A1 | 8/2000 |
| WO | 2003075395 A1 | 9/2003 |

* cited by examiner

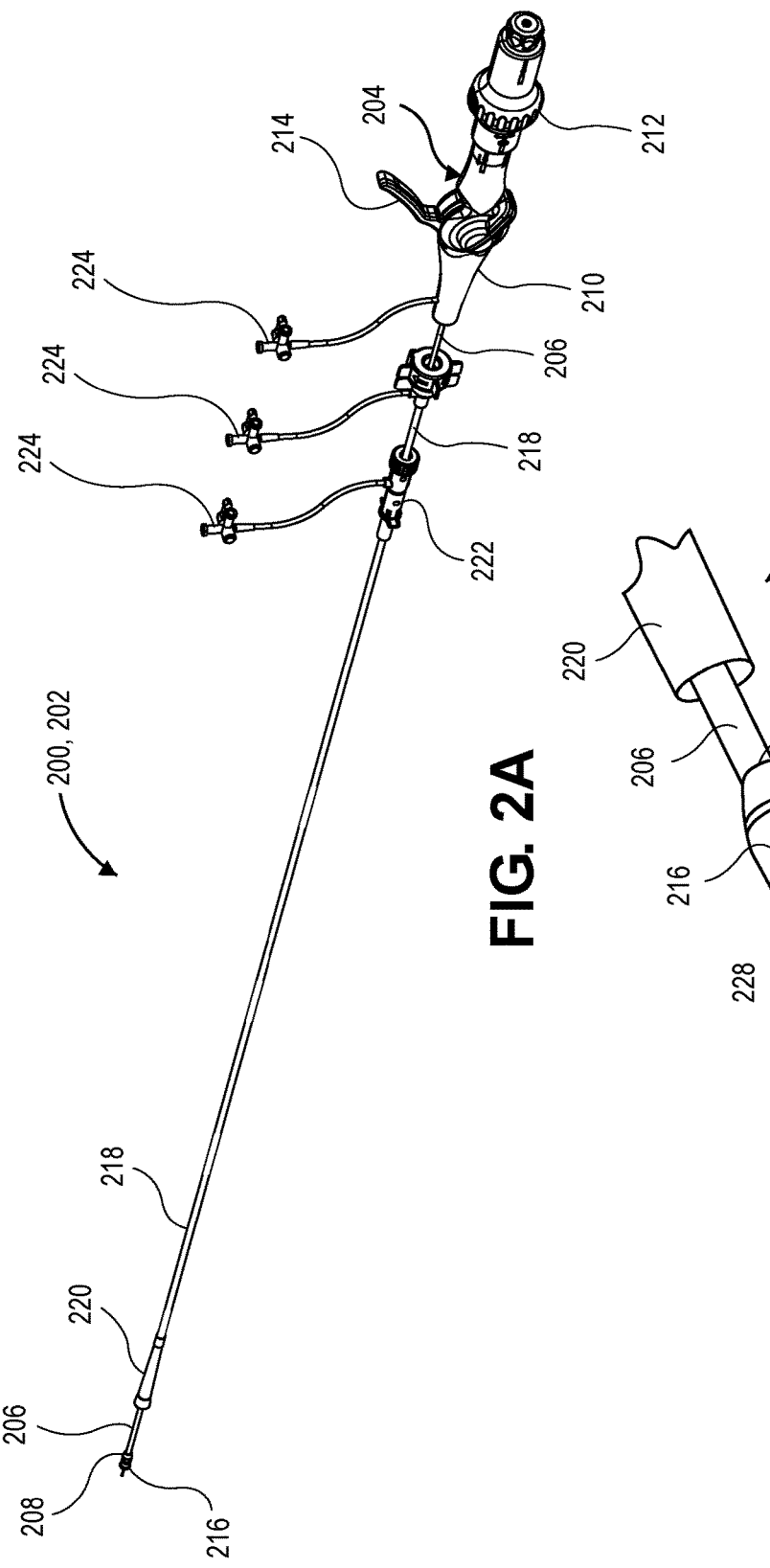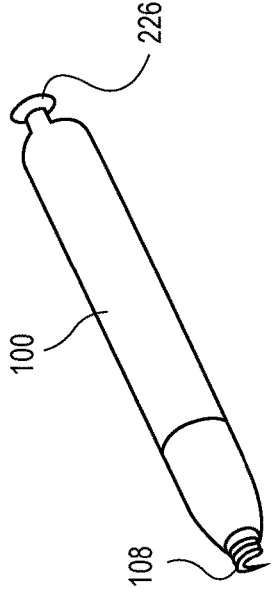
FIG. 2A
FIG. 2B

BIOSTIMULATOR HAVING PATCH ANTENNA

This application claims the benefit of priority of U.S. Provisional Patent Application No. 62/981,301, filed on Feb. 25, 2020, which is incorporated herein by reference in its entirety to provide continuity of disclosure.

BACKGROUND

Field

The present disclosure relates to biostimulators. More specifically, the present disclosure relates to leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Cardiac pacing by conventional pacemakers is usually performed by a pulse generator implanted subcutaneously or sub-muscularly in or near a patient's pectoral region, which delivers an electrical impulse to the heart via an elongated electrical lead implanted therein. Well known difficulties exist for conventional pacemakers, such as complex lead connectors and/or risks of mechanical failure of the leads. As a result, leadless cardiac pacemakers have been developed.

Leadless cardiac pacemakers are self-contained and self-sustainable biostimulators that can be attached to tissue within a dynamic environment. For example, leadless cardiac pacemakers can be implanted in chambers of the heart to deliver pacing pulses to target tissue. Leadless cardiac pacemakers can bidirectionally communicate with an external device, such as an external programmer, to exchange information, such as programming parameters, therapeutic data, patient and diagnostic event data. Leadless cardiac pacemakers may also communicate with other leadless pacemakers for multi-chamber pacing. Such communications are typically provided via a body channel network, e.g., by transferring signals directly through body tissue.

SUMMARY

Body channel network communication has drawbacks, such as the need for physical contact between a leadless cardiac pacemaker and body tissue, low data rate, high noise susceptibility, and a requirement for specialized readout devices (rather than readily available portable electronic devices, such as smart phones). To overcome these drawbacks, a wireless communication channel may be used instead of the body channel network. Given that the leadless cardiac pacemaker is a deep body implant, however, designing a wireless communication system is non-trivial because the leadless cardiac pacemaker is constrained by device volume, low battery capacity, and the implant location. To achieve effective wireless communication in leadless cardiac pacemakers, an antenna design is needed that is compact, biocompatible, and efficiently communicates signals from within the heart.

A biostimulator, e.g., a leadless cardiac pacemaker having a helical fixation element, including a patch antenna integrated into a housing is described below. In an embodiment, the patch antenna includes an annular wall. The annular wall may act as a ground plane of the patch antenna. The patch antenna also includes a dielectric layer, mounted on the annular wall, and a metal layer. The metal layer is embedded within the dielectric layer such that the dielectric layer surrounds the metal layer and separates the metal layer from the annular wall. The metal layer is a conductor of the patch antenna, and thus, is separated from the ground plane of the patch antenna by the dielectric layer.

An outer surface of the annular wall is at least a portion of a circular cylinder extending around a longitudinal axis. For example, the annular wall can be a circular cylinder forming a portion of a housing of the biostimulator. An inner surface of the dielectric layer can conform to the outer surface of the annular wall. For example, a cavity or a hole may be formed in the annular wall, and the dielectric layer may fill the cavity or the hole and conform to the outer surface within the cavity or the hole. In an embodiment, an exterior surface of the dielectric layer filling the cavity or the hole is at a same radial distance from the longitudinal axis as an outermost portion of the outer surface of the annular wall. Accordingly, the patch antenna can be flush with the outer surface of the annular wall to provide a compact form factor.

The metal layer of the patch antenna can include a trace extending over a length between a first end and a second end. Over a length of the trace, there may be several turnbacks. For example, the trace can be a meandering path that has turnbacks including longitudinally and circumferentially extending segments connected in an undulating pattern. Accordingly, the lengthy conductor can fit within the compact form factor of the patch antenna.

A signal may be fed to the conductor of the patch antenna from electronic circuitry within an electronics compartment of the biostimulator. The electronics compartment can be radially inward from the annular wall, along the longitudinal axis, and can feed the signal to the metal layer, as well as pacing pulses to an electrode of the biostimulator. In an embodiment, the signal is delivered through a feedthrough that interconnects the electronic circuitry to the metal layer. The feedthrough can include a feedthrough pin passing through the annular wall, and a feedthrough via electrically connected to the metal layer between the first end and the second end of the trace. The feedthrough via can be insulated by the dielectric layer radially between the trace and a feedthrough contact on the inner surface of the dielectric layer. The patch antenna may include a ground via electrically connected to the trace between the first end and the feedthrough via. The ground contact can extend from the trace through the dielectric layer to a ground contact on the inner surface of the dielectric layer. The feedthrough contact can be electrically connected to the feedthrough pin to receive the signal, and the ground contact can be electrically connected to the annular wall to ground the first end of the trace to the annular wall. In an embodiment, the patch antenna has a resonant frequency at a predetermined signal wavelength of the signal, and the length of the trace from the feedthrough via to the second end is one-quarter of the predetermined signal wavelength.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2B are perspective views of a biostimulator delivery system, in accordance with an embodiment;

DETAILED DESCRIPTION

Figure 1:
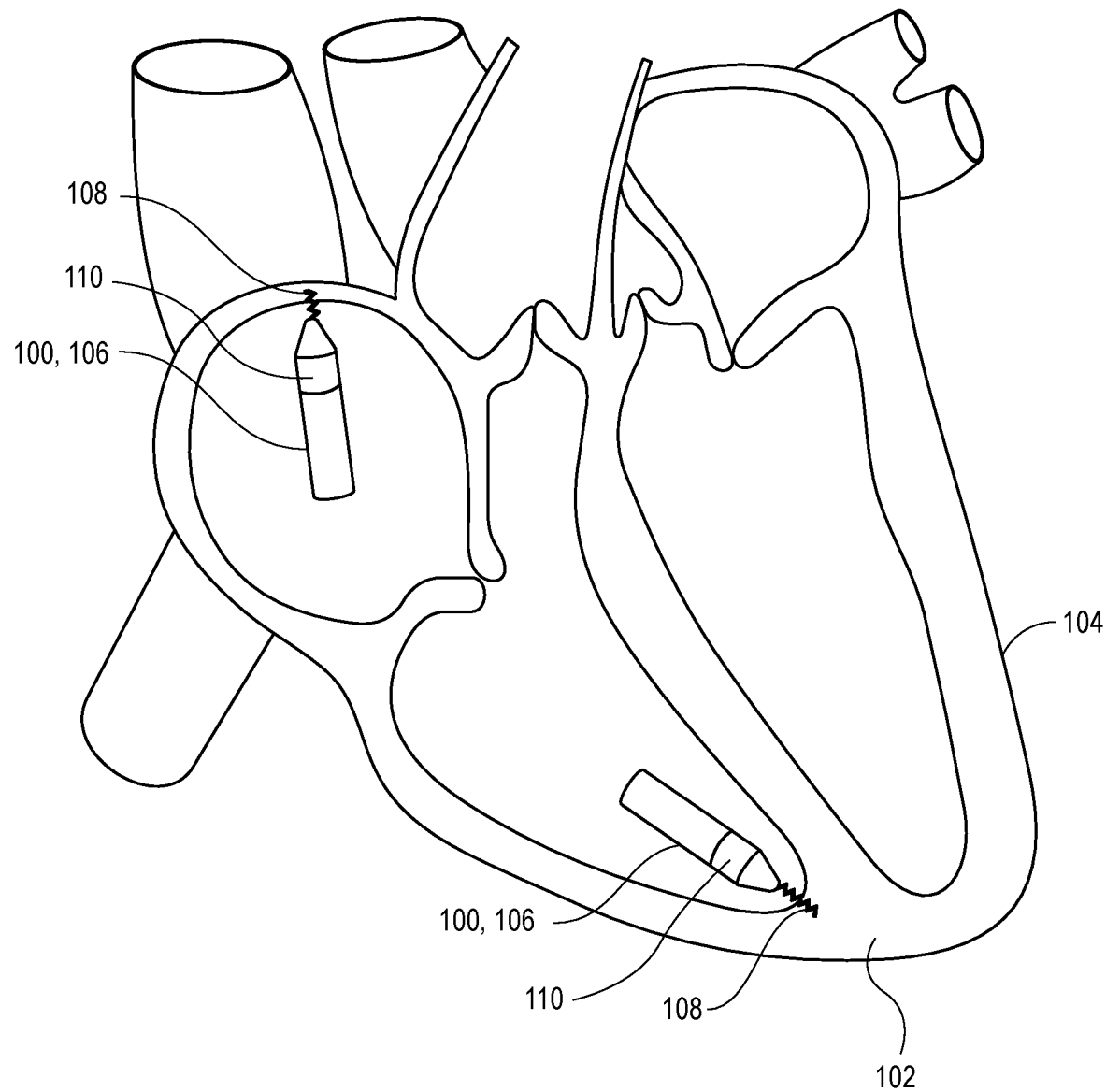
FIG. 1 is a diagrammatic medial-lateral cross section of a patient heart illustrating an example implantation of biostimulators in the patient heart, in accordance with an embodiment.

Embodiments describe a biostimulator having a patch antenna integrated into a housing. The biostimulator may be a leadless biostimulator, such as a leadless cardiac pacemaker used to pace cardiac tissue. The biostimulator may, however, be used in other applications, such as deep brain stimulation. Thus, reference to the biostimulator as being a cardiac pacemaker is not limiting. Furthermore, reference to a patch antenna as being incorporated into a biostimulator is not to be limiting of the patch antenna applicability. Whereas the patch antenna described below may be used in a biostimulator, e.g., integrated into a housing of the biostimulator, the annular structure of the patch antenna may make the antenna suitable for other applications. For example, the annular patch antenna could be incorporated into a cylindrical device housing, such as a barrel of a pen, to allow wireless communication between the cylindrical device and an external device, such as a smartphone. Notwithstanding the above, it will be appreciated that the patch antenna described below can provide particular advantages for deep body implants that require compact form factors, biocompatibility, and low-loss of near-field radiation.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes a patch antenna integrated into a housing. The patch antenna can have a ground plane provided by an annular wall of the housing. Thus, the patch antenna can be implemented without increasing a size or changing a form factor of the biostimulator. The patch antenna can have a conductor, e.g., a metal layer, embedded within a dielectric substrate, e.g., a dielectric layer, and the dielectric layer can be mounted on the annular wall. Thus, the conductor can be hermetically sealed within the dielectric substrate to reduce a likelihood of biological interaction between the conductor and the target tissue. Furthermore, the dielectric layer can encapsulate the metal layer, and the surrounding dielectric layer can have a thickness or a dielectric constant that reduces near-field radiation losses into the target tissue. Accordingly, the patch antenna and housing described below provides a compact, biocompatible, and efficient antenna that allows the biostimulator to effectively communicate via a wireless communication channel from an implant site within a patient to an external portable electronic device, such as a smartphone.

Referring to FIG. 1, a diagrammatic medial-lateral cross section of a patient heart illustrating an example implantation of biostimulator in the patient heart is shown in accordance with an embodiment. A cardiac pacing system includes one or more biostimulators 100. The biostimulator(s) 100 can be implanted at respective target sites in a patient. For example, the biostimulator(s) 100 can be implanted within a target tissue 102 in a heart 104 of the patient.

The biostimulator(s) 100 can be leadless biostimulators, such as leadless cardiac pacemakers 106. Each biostimulator 100 can be placed in a cardiac chamber, such as a right atrium and/or right ventricle of the patient heart 104, or attached to an inside or outside of the cardiac chamber. Attachment of the biostimulator 100 to the target tissue 102 can be accomplished via one or more fixation elements 108, such as helical anchors. In a particular embodiment, the leadless pacemaker can use two or more electrodes located on or within a housing 110 of the leadless pacemaker for pacing the cardiac chamber upon receiving a triggering signal from internal circuitry and/or from at least one other device within the body.

The biostimulator(s) 100 may be capable of communicating with each other or with an external device using a wireless communication channel. For example, as described below, a patch antenna (FIG. 4) may be integrated into the housing 110 to enable communication circuitry within the housing to implement a communication protocol for communicating with a remote monitoring device, e.g., a portable electronic device such as a smartphone, tablet, wearable device, etc. In an embodiment, the communication circuitry implements a Bluetooth Low Energy (BLE) communication protocol that operates at 2.4-2.48 GHz. The BLE communication protocol is reliable and cost-effective, and thus, the biostimulator(s) 100 can effectively communicate with the remote monitoring device over the wireless communication channel.

Referring to FIG. 2A, a perspective view of a biostimulator transport system is shown in accordance with an embodiment. A biostimulator transport system 200 may be used for delivery and/or retrieval of the biostimulator 100, e.g., a leadless pacemaker, into or from a patient. For example, the biostimulator transport system 200 can be a biostimulator delivery system 202 used for delivery of the biostimulator 100 into a patient.

The biostimulator transport system 200 can include a handle 204, and an elongated catheter 206 extending distally from the handle 204 to a distal catheter end 208. The handle 204 can include several portions, e.g., a distal handle portion 210 and a proximal handle portion 212, and features that allow a user to provide inputs at a proximal end of the system that translate to outputs at the distal end of the system. For example, the elongated catheter 206 can be a deflectable catheter, and an operator can use the handle 204 to steer the distal catheter end 208 in the patient.

In an embodiment, the handle 204 includes a deflection lever 214 that can be used to deflect the distal catheter end 208. By pivoting the deflection lever 214 toward the distal handle portion 210 of the handle 204, the operator can cause a pull ring assembly extending within the elongated catheter 206 to apply off-axis compression to the elongated catheter 206, resulting in lateral deflection of the distal catheter end 208.

The handle 204 can be used to apply a torque to a docking cap 216 at the distal catheter end 208 of the system. In an embodiment, the proximal handle portion 212 can be rotationally and/or longitudinally moveable relative to the distal handle portion 210. For example, the distal handle portion 210 can be coupled to the elongated catheter 206 and the proximal handle portion 212 can be coupled to a torque shaft extending within the elongated catheter 206. The docking cap 216 can be mounted on the torque shaft. Accordingly, an operator can rotate the proximal handle portion 212 relative to the distal handle portion 210 to impart torque to the torque shaft. The torque can cause the docking cap 216, which is rotationally linked to the proximal handle portion 212 through the torque shaft, to rotate relative to the elongated catheter 206, which is rotationally linked to the distal handle portion 210.

In an embodiment, the biostimulator transport system 200 includes a protective sheath 218 mounted on the elongated catheter 206. The protective sheath 218 can be slidably disposed on the elongated catheter 206. The protective sheath 218 can include an atraumatic end 220, e.g., a soft, funnel-shaped distal portion, that can slide distally over the distal catheter end 208 of the elongated catheter 206 and/or the biostimulator 100 (not shown). The atraumatic end 220 can have an outer dimension, which may be larger than a proximal portion of the protective sheath 218. For example, the atraumatic end 220 may flare in a distal direction to a funnel opening that can advance over a docking cap 216 of the biostimulator transport system 200. An outer dimension of the atraumatic end 220 can be larger than a region of the protective sheath 218 supporting a valve bypass tool 222.

The valve bypass tool 222 can be slidably disposed on the protective sheath 218 such that a distal portion of the valve bypass tool 222 can slide distally over the distal catheter end 208 of the elongated catheter 206 and/or the atraumatic end 220 of the protective sheath 218. More particularly, the valve bypass tool 222 can be inserted into an access introducer (not shown) to gain access to the patient vasculature, and after access is established, the distal portion of the protective sheath 218 and/or the distal end of the elongated catheter 206 can be advanced through the valve bypass tool 222 into the patient.

The valve bypass tool 222, the protective sheath 218, and the elongated catheter 206 can have respective flush ports 224 extending respectively therefrom. Each of the longitudinal bodies are displaceable proximal-distal relative to each other, and thus, the flush ports 224 can be used to introduce and/or flush saline or other fluids between the longitudinal bodies or through the respective components in different relative positions.

Referring to FIG. 2B, a distal perspective view of a biostimulator transport system having a docking cap to receive a biostimulator is shown in accordance with an embodiment. The distal catheter end 208 of the elongated catheter 206 may be selectively connectable to the biostimulator 100. More particularly, the biostimulator 100 can be mounted on the distal catheter end 208 of the elongated catheter 206. In an embodiment, the biostimulator 100 includes an attachment feature 226 that docks within or onto the docking cap 216. The attachment feature 226 can include a channel (not shown) shaped and sized to receive one or more tethers 228. The tethers 228 can comprise wires, shafts, tubes, cords, ropes, strings, or other similar structures that can extend throughout the catheter shaft. For example, the tethers 228 can extend through a shaft lumen of a torque shaft assembly. In some embodiments, the tethers 228 comprise a shape memory material, such as nickel-titanium. In other embodiments, the tethers 228 comprise stainless steel wires or braids. The tethers 228 can be inserted into and locked within the attachment feature 226 to connect the biostimulator 100 to the biostimulator transport system 200.

When the tethers 228 are locked within the attachment feature 226, the tethers 228 can be retracted to pull the biostimulator 100 toward the docking cap 216. The docking cap 216 can include a docking cavity 230 having a shape and size to receive the attachment feature 226 of the biostimulator 100. As the biostimulator 100 moves toward the docking cap 216, the attachment feature 226 can insert into the docking cavity 230. Accordingly, the docking cavity 230 can receive the attachment feature 226 to dock the biostimulator 100 to the biostimulator delivery system 202 for delivery to the patient.

Torque can be transmitted from the docking cap 216 to the biostimulator 100 via the torque shaft when the attachment feature 226 is received in the docking cap 216. More particularly, the torque shaft can be rotated in a first direction, e.g., clockwise, to transmit torque through the docking cap 216 to the attachment feature 226, and to cause the fixation element 108 to engage and screw into the target tissue 102.

The biostimulator 100 can be protected by the atraumatic end 220 of the protective sheath 218 during delivery and/or retrieval of the biostimulator 100 from the patient. The atraumatic end 220 can have a braided or woven tubular construction. The atraumatic end 220 can therefore be advanced over the biostimulator 100 and may expand radially over the biostimulator 100 in the case where an outer dimension of the biostimulator 100 is greater than the inner diameter of the atraumatic end 220. Accordingly, the atraumatic end 220 can cover the biostimulator 100 to protect the biostimulator 100 during advancement into the patient.

Figure 3A:
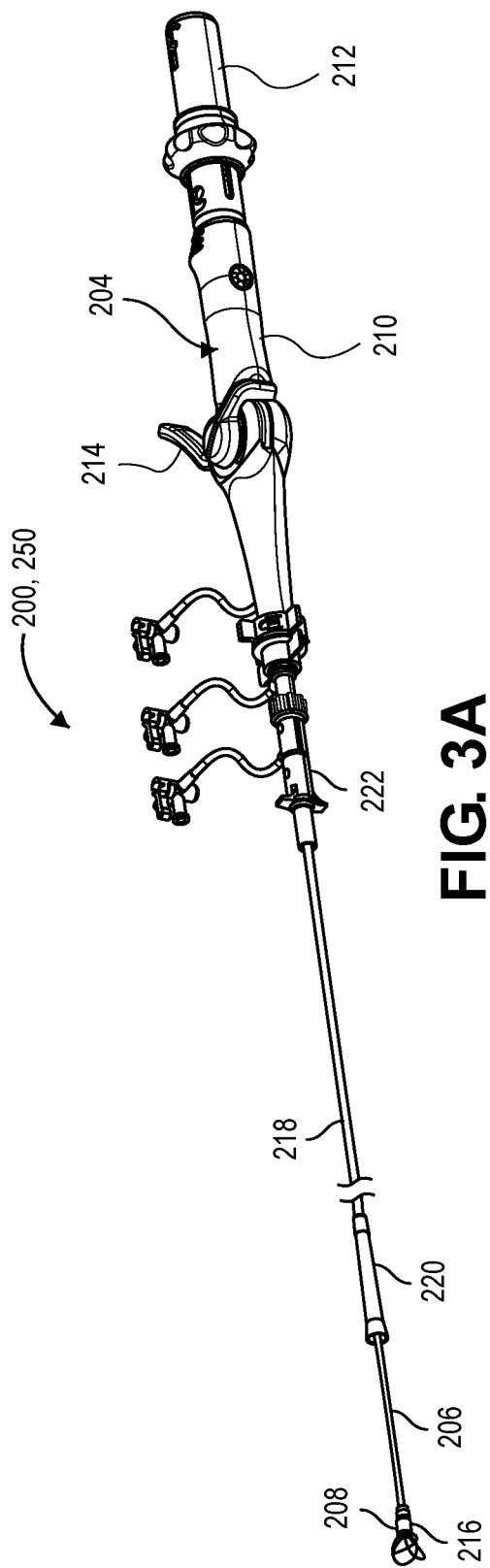
FIGS. 3A-3B are perspective views of a biostimulator retrieval system, in accordance with an embodiment.

Referring to FIG. 3A, a perspective view of a biostimulator retrieval system 250 is shown in accordance with an embodiment. The biostimulator transport system 200 may be a biostimulator retrieval system 250. The biostimulator retrieval system 250 can be used to explant one or more biostimulator 100 from the atrium and/or the ventricle of the heart 104 of the patient. Removal and retrieval of the biostimulator(s) 100 may be accomplished endocardially. For example, the torque shaft of the elongated catheter 206 can be rotated in a second direction, e.g., counterclockwise, to disengage the biostimulator 100 from the target tissue 102. Accordingly, the biostimulator retrieval system 250 shown in FIG. 3A can have a structure similar to that shown and described with respect to the biostimulator delivery system 202 of FIG. 2A to retrieve the biostimulator 100 from a target anatomy. The similarly numbered components of the biostimulator retrieval system 250 are not described again here in the interest of brevity.

Figure 3B:
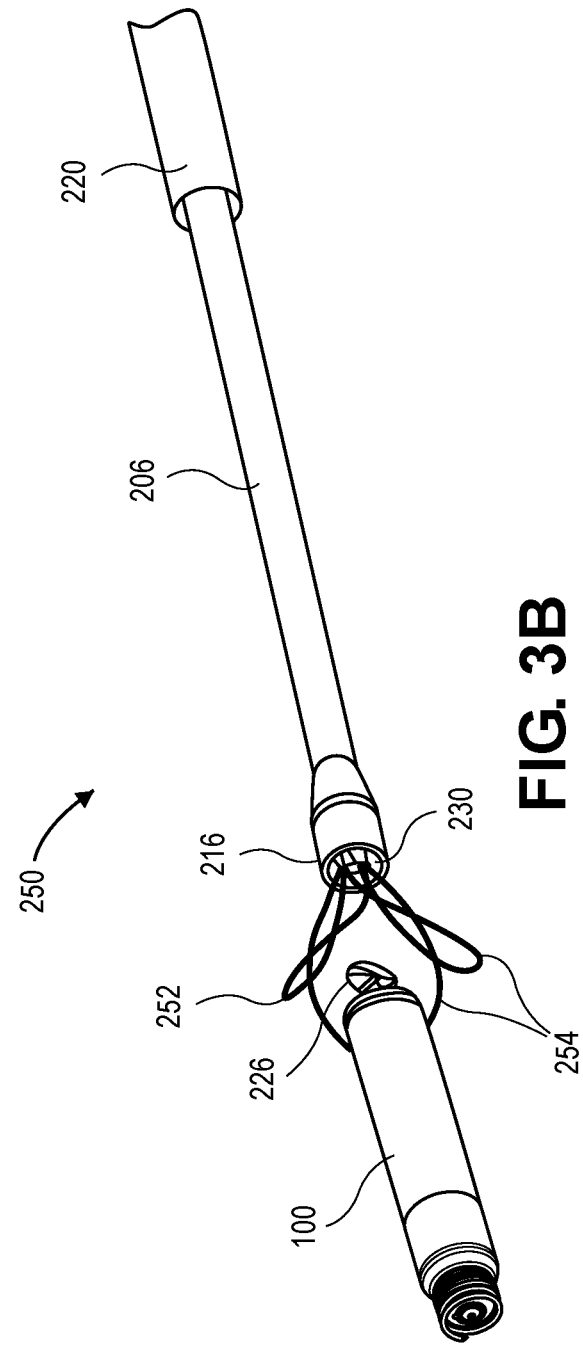

Referring to FIG. 3B, a perspective view of a distal portion of a biostimulator retrieval system prior to attaching to a biostimulator is shown in accordance with an embodiment. The distal portion of the biostimulator retrieval system 250 can include features to engage the biostimulator 100 to facilitate capturing and unscrewing the biostimulator 100 from the target tissue 102. More particularly, the biostimulator retrieval system 250 can include a snare 252 extending through the elongated catheter 206 to grasp the biostimulator 100 or other medical device. The snare 252 can include at least one snare loop 254, e.g., a wire loop, extending from the elongated catheter 206. As the snare 252 is advanced distally out of the biostimulator retrieval system 250 from the docking cap 216, the loop(s) can expand in size to aid a user in positioning the snare 252 around or in proximity to the biostimulator 100 to be retrieved. In some implementations, as in FIG. 3B, the snare 252 can include multiple loops, such as three loops. However, any number of loops can be used as long as the elongated catheter 206 contains sufficient volume to accommodate the loops.

The distal portion of the retrieval catheter can include the docking cap 216 configured to allow docking of the leadless pacemaker with the biostimulator retrieval system 250 after engaging the pacemaker with the snare 252. A user can transmit torque through the torque shaft via the handle 204 to rotate the docking cap 216 relative to the elongated catheter 206. More particularly, the torque shaft can extend through the length of the catheter to the handle 204, e.g., the proximal handle portion 212, which is coupled to the torque shaft. Rotation or actuation of the handle 204 rotates the torque shaft, thereby rotating the docking cap 216 at the end of the retrieval catheter. The protective sheath 218 can be positioned along the elongated catheter 206, and can be advanced or retracted to cover or expose the docking cap 216 and the leadless pacemaker using the atraumatic end 220.

During retrieval, the biostimulator retrieval system 250 can be navigated through the patient to the implant site. The snare 252 can be placed over the attachment feature 226 and the loops of the snare 252 can be reduced in size, thereby grasping or locking onto the attachment feature 226 of the pacemaker. Following capture and locking of the snare 252 with the leadless pacemaker, the biostimulator 100 may be docked within the docking cap 216. More particularly, the attachment feature 226 of the biostimulator 100 can be pulled into the docking cavity 230 of the docking cap 216. In some implementations, the docking cap 216 can include a key or interference feature configured to mate with and engage a corresponding key or feature on the biostimulator 100. In some implementations, the key or slot on the docking cap 216 can match a unique shape or feature of the attachment feature 226 of the pacemaker. Because the key or slot on or in the docking cap 216 can mate with and engage the attachment feature 226 of the pacemaker, the retrieval catheter can be configured to apply torque to the pacemaker to unscrew and remove the pacemaker from tissue.

Figure 4:
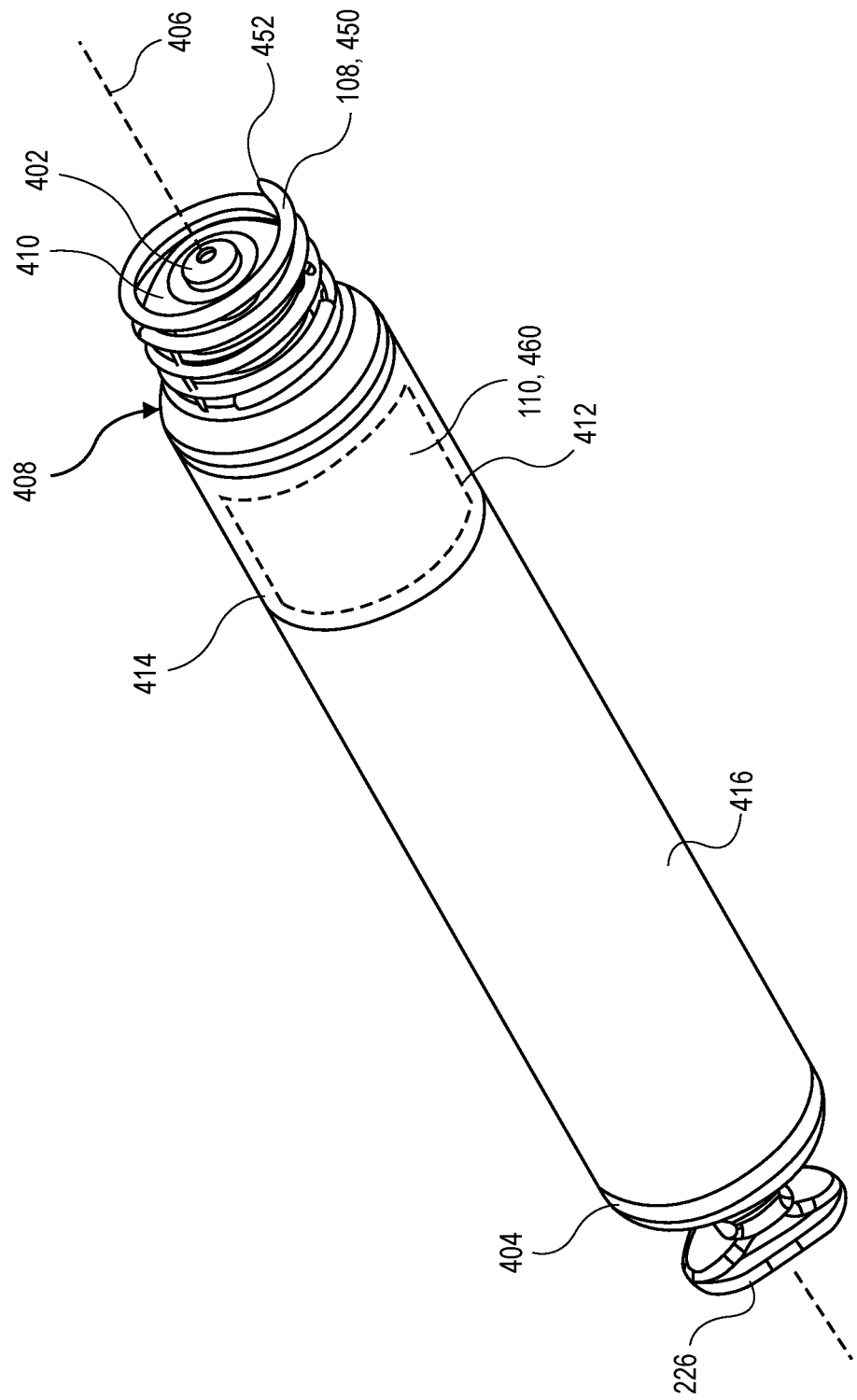
FIG. 4 is a perspective view of a biostimulator having a patch antenna integrated into a housing, in accordance with an embodiment.

Referring to FIG. 4, a perspective view of a leadless biostimulator is shown in accordance with an embodiment. A biostimulator 100 can be a leadless biostimulator, e.g., a leadless cardiac pacemaker 106 used to deliver pacing impulses to the atria or ventricles of a heart 104. The biostimulator 100 can include the housing 110 having electrodes. For example, the biostimulator 100 includes each of a distal electrode 402 and a proximal electrode 404 disposed on or integrated into the housing 110. The distal electrode 402 and the proximal electrode 404 can be used to sense and pace the heart 104. The electrodes can be integral to the housing 110 or connected to the housing 110, e.g., at a distance of less than several centimeters from the housing.

In an embodiment, the housing 110 contains an energy source (not shown) to provide power to the pacing electrodes. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing 110 can have a longitudinal axis 406, which may be an axis of symmetry along which several other biostimulator components are disposed. For example, a header assembly 408 can be mounted on a distal end of the housing 110 along the longitudinal axis 406. The header assembly 408 can include an electrical feedthrough assembly (for electrical stimulation), incorporating a helix mount 410 and the fixation element 108 mounted on the helix mount 410.

In an embodiment, the fixation element 108 includes a helix 450. For example, the helix 450 can include a helically-formed wire extending about the longitudinal axis 406 to a piercing tip 452. The piercing tip 452 can have a sharpened point to pierce the target tissue 102. The helix mount 410 may have a threaded outer surface to receive the helix 450. For example, a proximal end of the helix 450 can engage the external thread of the helix mount 410 and be screwed onto the helix mount 410 to fasten the helix 450 to the housing 110. An adhesive can be used to bond the helix 450 to the helix mount 410 to further secure the helix 450 to the housing 110. Accordingly, the helix 450 can be rigidly secured to the housing 110 via the helix mount 410. Other joining technologies, such as potting or ultrasonic welding, along with joint designs common to such technologies, may be used to mate the components.

It will be appreciated that the helix 450 is provided as a non-limiting example of the fixation element 108 that can be used to secure the housing 110 to the target tissue 102. Other fixation mechanisms, such as hooks, barbs, adhesives, etc., may be incorporated at the distal end of the housing 110 and/or on the helix mount 410 to anchor the biostimulator 100 to the target tissue 102 at the target site. Furthermore, the biostimulator 100 can include several fixation elements 108. For example, whereas a single helical fixation element 108 is illustrated in FIG. 4, the biostimulator 100 can include additional fixation elements 108, e.g., additional helices, barbs, etc.

The header assembly 408 can also include the distal electrode 402. The assembled components of the header assembly 408 can provide a distal region of the biostimulator 100 that attaches to the target tissue 102, e.g., via engagement of the fixation element 108 with the target tissue 102. When engaged, the distal region can deliver a pacing impulse to the target tissue 102, e.g., via the distal electrode 402 that is held against the target tissue 102 by the fixation element 108.

The housing 110 can have an electronics compartment 412 (shown by hidden lines). More particularly, the electronics compartment 412 can be a cavity laterally surrounded by a housing wall, e.g., an annular wall 414. The annular wall 414 can extend around the longitudinal axis 406 to define the electronics compartment 412. For example, the annular wall 414 can have a cylindrical interior surface defining a cylindrical electronics compartment 412.

The annular wall 414 can include a conductive, biocompatible, inert, and anodically safe material such as titanium, 316L stainless steel, or other similar materials, to laterally enclose the electronics compartment 412 between the energy source of the biostimulator 100 within a proximal portion of the housing 110, and the header assembly 408 at the distal portion of the biostimulator 100. More particularly, a proximal end of the annular wall 414 can be mounted on an energy source container 416 to proximally enclose the electronics compartment 412 and the header assembly 408 can be mounted on a distal end of the annular wall 414 to distally enclose the electronics compartment 412. Accordingly, the header assembly 408, the annular wall 414, and the energy source container 416 can surround a volume of the electronics compartment 412.

In one implementation, the electronics compartment 412 contains an electronics assembly (not shown). The electronics assembly can be mounted in the electronics compartment 412 and can include electronic circuitry within the electronics compartment 412. For example, the electronics assembly can include, without limitation, a flexible circuit or a printed circuit board having electrical connectors that connect to electrical pins of the header assembly 408 and the energy source. The electronic circuitry of the electronics assembly has one or more electronic components mounted on a substrate. For example, the electronic circuitry can include one or more processors, capacitors, resistors, inductors, switches, etc., interconnected by electrical traces, vias, or other electrical connectors. The electronic circuitry can be configured to perform sensing and pacing of the target tissue 102. The electronic circuitry may also send or receive wireless communication signals through an antenna incorporated into the housing 110, as described below.

In an embodiment, the housing 110 incorporates a patch antenna 460. More particularly, the annular wall 414 of the housing 110 can provide a ground plane of the patch antenna 460, and several other components mounted on the annular wall 414 can provide a dielectric substrate and a conductor of the patch antenna 460. The annular wall 414, as described below, can therefore function both to contain the electronic circuitry used to communicate wirelessly with external devices and facilitate such communication via radiated wireless signals. By fulfilling this dual-purpose in a compact form factor, the housing 110 achieves effective wireless communication from an implantable biostimulator 100.

Figure 5:
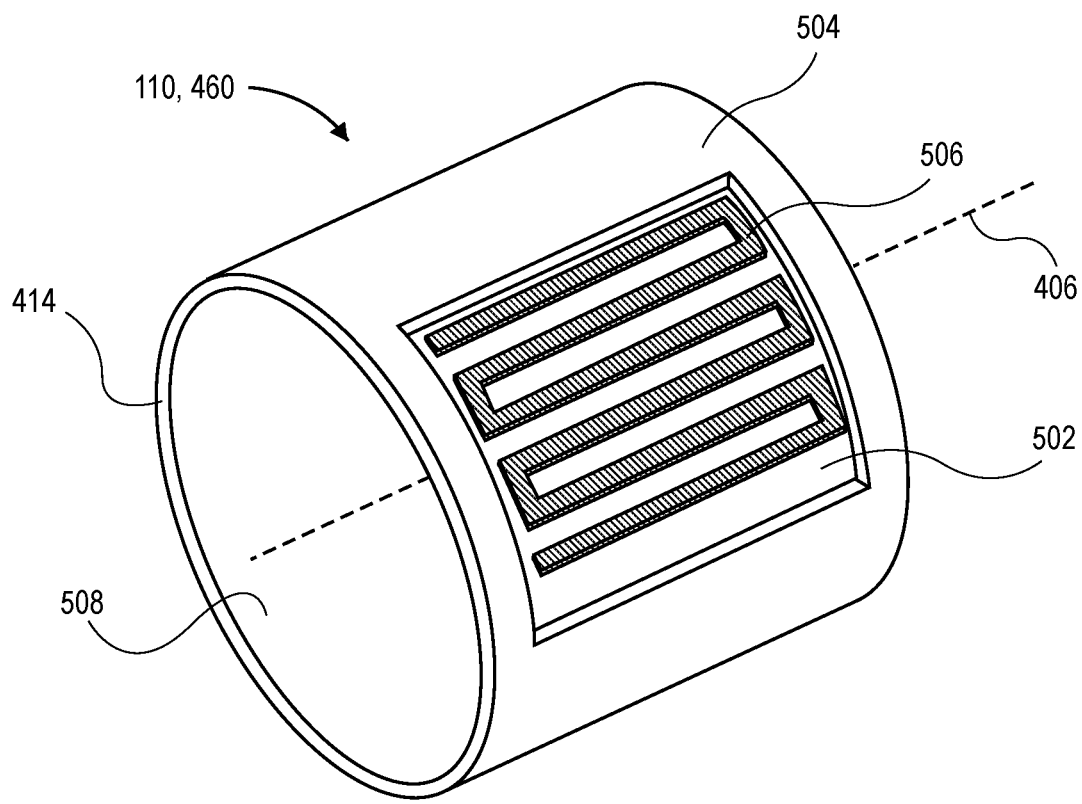
FIG. 5 is a perspective view of a patch antenna, in accordance with an embodiment.

Referring to FIG. 5, a perspective view of a patch antenna is shown in accordance with an embodiment. The patch antenna 460 can be integrated into the portion of the housing 110 of the biostimulator 100 that is between the header assembly 408 and the energy source container 416, as described above. Alternatively, rather than being mounted on the annular wall 414 that defines the electronics compartment 412, the patch antenna 460 may be integrated within the header assembly 408, the energy source container 416, or another component of the biostimulator 100. Furthermore, the patch antenna 460 may be used in another device that requires an antenna having an annular form factor. For example, the patch antenna 460 could be integrated into a barrel of a pen. In any case, the patch antenna 460 can have a layer of dielectric material sandwiched between several metallic layers. In an embodiment, the patch antenna 460 includes the annular wall 414 as one of the metallic layers to provide a ground plane of the patch antenna 460. The dielectric material and the other metallic layer can be provided by components coupled to the annular wall 414, to form an antenna that radiates with respect to the ground plane.

In an embodiment, the patch antenna 460 includes a dielectric layer 502 (FIG. 6) integrated onto or into the annular wall 414. The dielectric layer 502 is rendered transparently in FIG. 5 to allow a metal layer 506 to be seen, however, the dielectric layer 502 can fill the recess shown. For example, the dielectric layer 502 may be mounted on the annular wall 414, e.g., within the illustrated recess. The dielectric layer 502 can be placed on an outer surface 504 of the annular wall 414. As described below, the dielectric layer 502 can be, but is not necessarily, recessed at least partially below the outer surface 504. The dielectric layer 502 may be coupled to the annular wall 414 in other manners. For example, the dielectric layer 502 may fill a hole passing through the annular wall 414. In any case, the dielectric layer 502 can provide a dielectric substrate of the patch antenna 460.

The dielectric layer 502 may be formed from a dielectric material. For example, the dielectric layer 502 can be formed from a ceramic, such as metal oxide or silicon, or a polymer, such as polyimide, kapton, or parylene. These materials are provided by way of example, however, and the dielectric layer 502 may be formed from any electrically insulative material. When formed from a ceramic, the dielectric layer 502 may alternatively be referred to as a ceramic layer. When formed from a polymer, the dielectric layer 502 may alternatively be referred to as a polymer layer. Whether referred to as a ceramic layer or a polymer layer, however, the dielectric layer 502 is a dielectric material separating the metallic layers of the patch antenna 460.

Figure 6:
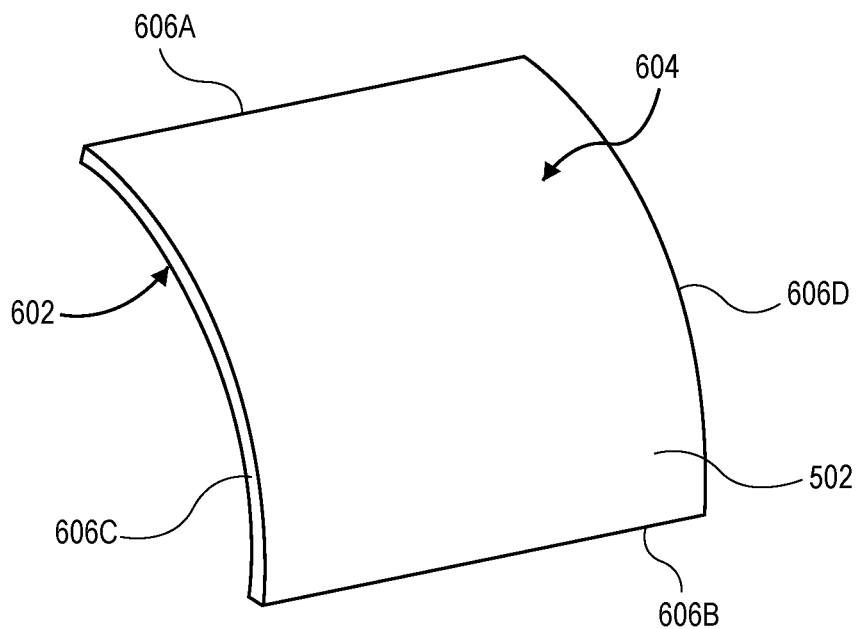
FIG. 6 is a perspective view of a dielectric layer of a patch antenna, in accordance with an embodiment.

The other metallic layer (other than the ground plane) of the patch antenna 460 may be a metal layer 506. The metal layer 506 can include one or more layers of metals. For example, the metal layer 506 may have a layer of platinum laminated or apposed to a layer of nickel. The layer of nickel can be used as an intermediate for bonding purposes. More particularly, the layers can be selected to provide for robust interlayer adhesion between the metal layer 506 and the dielectric layer 502. In an embodiment, the metal layer 506 is embedded within the dielectric layer 502 such that the dielectric layer 502 surrounds the metal layer 506 (FIG. 6). The dielectric layer 502 shown in FIG. 5 is rendered transparently to allow the metal layer 506 to be seen, however, the dielectric layer 502 can surround the metal layer 506. Accordingly, the metal layer 506 may be contained and hidden by the dielectric layer 502, and may not be exposed to view through the dielectric layer 502. The metal layer 506 can provide a conductor of the patch antenna 460.

It will be appreciated that the metal layer 506 may or may not be completely surrounded by the dielectric layer 502. For example, the dielectric layer 502 may partially surround the metal layer 506, allowing one or more surfaces of the metal layer 506 to be exposed from the dielectric layer 502. In an embodiment, a surface of the metal layer 506 is co-radial (at a same radial location relative to a central axis of the device) with a surface of the dielectric layer 502. For example, an outermost surface of the metal layer 506 may be co-radial with an outermost surface of the dielectric layer 502. Optionally, a coating, such as a thin parylene coating, may be applied over the outermost surfaces to enclose the metal layer 506 between the coating and the dielectric layer 502.

In an embodiment, an electrical via can feed a signal through the dielectric layer 502 to the metal layer 506. For example, the electrical via can be formed vertically above (or radially outward) from the ground plane to carry the signal to the metal layer 506 through the dielectric layer 502. The dielectric layer 502 can insulate the via. The signal can be fed through the ground plane at a discrete location through a feedthrough pin, as described below. Thus, the signal can be generated within the electronics compartment 412 and passed radially outward to the metal layer 506.

In an embodiment, the structures of the patch antenna 460 are constructed using semiconductor processing or other surface modification technologies. For example, any cavities or holes, such as the recessed cavity for the dielectric layer 502, the feedthrough holes in the ground plane or the dielectric layer 502, etc., can be manufactured by electrochemical etching or ion beam ablation or other etch technologies. Dielectric materials, such as the dielectric layer 502 or a dielectric sleeve surrounding a feedthrough pin in the ground plane, as described below, may be formed using dielectric layer deposition techniques, including physical vapor deposition (PVD), chemical vapor deposition (CVD), or other deposition means. Similarly, conductive materials, such as the feedthrough pin in the ground plane, the feedthrough passing through the dielectric layer 502, or the metal layer 506 embedded in the dielectric layer 502, may be manufactured by PVD, CVD, sputtering, ion beam deposition or other deposition means.

The annular wall 414 of the patch antenna 460 provides an isodiametric antenna structure that is revolved about the longitudinal axis 406. The annular wall 414 can have the outer surface 504 extending longitudinally from a proximal end to a distal end parallel to an interior surface 508. The interior surface 508 can be a circular cylinder. Similarly, the outer surface 504 of the annular wall 414 can be at least a portion of a circular cylinder. More particularly, the region of the outer surface 504 that is circumferentially offset from the dielectric layer 502 may be a same radial distance from the longitudinal axis 406, and thus, may provide the portion of the circular cylinder. By contrast, a region of the outer surface 504 that is recessed to receive the dielectric layer 502 (and thus radially below the dielectric layer 502) may be a different radial distance from the longitudinal axis 406, and thus, may be at least a portion of another circular cylinder. In other words, the outer surface 504 may include a circular cylinder having a recessed region radially inward from an outermost region.

Referring to FIG. 6, a perspective view of a dielectric layer of a patch antenna is shown in accordance with an embodiment. The dielectric layer 502 can be a curved dielectric layer that fits into the recessed region of the outer surface 504 of the annular wall 414. As such, the dielectric layer 502 can have an inner surface 602 that conforms to the outer surface 504 of the annular wall 414. More particularly, the recess region of the outer surface 504 may have a radial distance from the longitudinal axis 406, and the inner surface 602 of the dielectric layer 502 may be a concave surface having a radius equal to the radial distance. Accordingly, the curved inner surface 602 can mesh with and fit tightly against the outer surface 504 of the annular wall 414.

Similar to the cylindrical wall of the housing 110, the dielectric layer 502 can have an exterior surface 604 extending in a longitudinal and circumferential direction parallel to the inner surface 602. The dielectric layer 502 may be a section of a cylinder, and therefore, may be referred to as being a cylindrical arc section. The cylindrical arc section can be defined by the exterior surface 604, the inner surface 602, and one or more lateral edges 606 extending around the exterior and inner surfaces 602. The exterior and inner surfaces 602 can both be rectangular areas curved about the longitudinal axis 406, and thus, can extend from a first lateral edge 606A to a second lateral edge 606B in a circumferential direction about the longitudinal axis 406, and from a third lateral edge 606C to a fourth lateral edge 606D in a longitudinal direction parallel to the longitudinal axis 406.

The rectangular profile of the patch antenna 460 is provided by way of example, and the patch antenna may have other profile shapes. For example, the patch antenna 460 could have a triangular profile shape between three lateral edges, or an elliptical profile shape enclosed within a single oval lateral edge. In any case, the profile shape can be curved about the central axis of the device such that the patch antenna 460 has the curved inner surface 602 to conform to the outer surface 504 of the annular wall 414.

Figure 7:
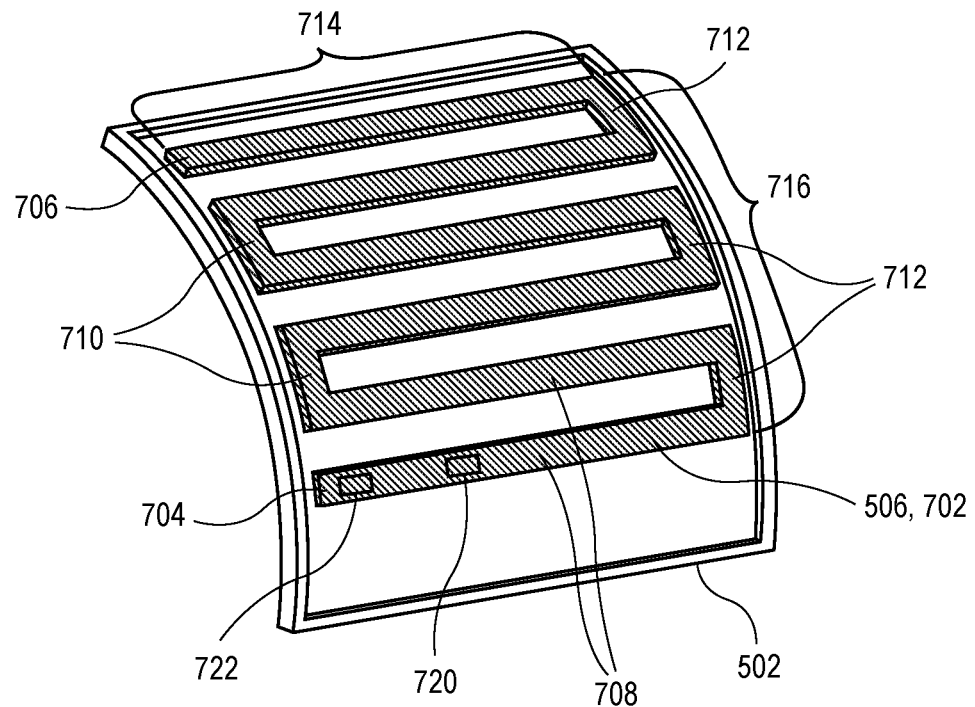
FIG. 7 is a top cutaway view of a trace embedded in a dielectric layer of a patch antenna, in accordance with an embodiment.

Referring to FIG. 7, a top cutaway view of a trace embedded in a dielectric layer of a patch antenna is shown in accordance with an embodiment. Removing material from the exterior surface 604 in a radially inward direction exposes the metal layer 506 embedded within the dielectric layer 502. In an embodiment, the metal layer 506 is a single-plate meandered patch antenna layer. More particularly, the metal layer 506 may include a trace 702 extending over an undulating path from a first end 704 to a second end 706. The trace 702 can extend over a length measured along the undulating path. More particularly, the undulating path can have longitudinal segments 708 interconnected with each other by circumferential segments 710. The interconnection of a pair of longitudinal segments 708 by a circumferential segment 710 creates a turnback 712 in the undulating path. More particularly, the turnback 712 is a reversal in direction of the trace 702 as the trace traverses along the length between the first end 704 and the second end 706. The trace 702 includes several turnbacks 712 to create an undulating path having the required length that fits within the compact cylindrical arc section of the dielectric layer 502. More particularly, the trace 702 can have a trace longitudinal width 714 that is less than a longitudinal dimension of the dielectric layer 502, and the trace 702 may have a trace circumferential width 716 that is less than a circumferential dimension of the dielectric layer 502.

Figure 11:
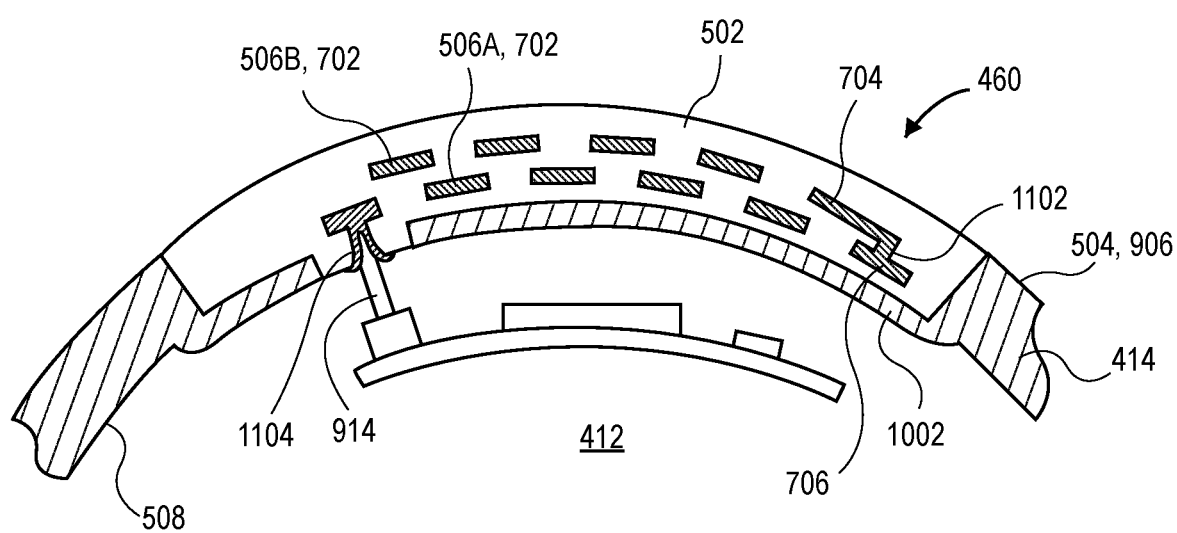
FIG. 11 is a sectional view of a patch antenna, in accordance with an embodiment.

A length of the trace 702 can also be increased by forming the trace 702 from several stacked trace segments that are stacked between the inner surface 602 and the exterior surface 604 (FIG. 11). For example, the trace 702 illustrated in FIG. 7 can be a first trace segment or layer and one or more additional trace segments or layers can be stacked on the first trace segment in a radial direction. For example, the trace segments be stacked such that each trace segment is at a different radial distance from the longitudinal axis 406. The trace segments can be insulated from each other by intervening dielectric layers. For example, each trace segment can be separated from an adjacent trace segments by a dielectric layer that is positioned radially between the trace segments. In an embodiment, the end of the first trace segment can be electrically connected to a start of an adjacent second trace segment. The electrical interconnection may be provided by an electrical via, formed vertically (or radially) between the end of the first trace segment and the start of the second trace segment. The second and subsequent trace segments may similarly be connected to adjacent trace segments by interconnecting vias. The interconnected trace segments provide a lengthened trace path for the combined stack, which represents an overall trace 702 for the patch antenna 460. Accordingly, although circumferential space is limited, the traces 702 can be stacked radially to increase the overall trace 702 length. In such case, the overall trace 702 length is determined by the stacked undulating path formed by multiple layers of dielectric and metallic deposition.

The metal layer 506 can be a thin-film curved metallic layer having the undulating pattern described above. In an embodiment, the metal layer 506 is fabricated from platinum, which provides low radiation loss and is biocompatible. Other materials, however, may be used to form the metal layer 506. In an embodiment, the trace 702 is patterned on the ceramic substrate, e.g., via metal deposition processes. Alternatively, the trace 702 may be fabricated by cutting the undulating pattern from a metallic film. The patterned trace 702 can then be embedded within the dielectric layer 502 during a ceramic fabrication process. For example, the dielectric layer 502 may include several layers that are built on top of each other during a Low Temperature Cofired Ceramic (LTCC) process. The trace 702 may be sandwiched between the dielectric layers 502 as the layers are built up such that the trace 702 becomes encapsulated within the dielectric layer 502 after the layers are sintered.

The patch antenna 460 operates on the principle of radiating signals from the metal layer 506 (the conductor) with respect to the annular wall 414 (the ground plane). More particularly, an electrical signal can be fed to the metal layer 506 such that horizontal components of the fringing fields at the edges of the trace 702 add up in phase and radiate. Accordingly, the patch antenna 460 can include electrical interconnections to feed the electrical signal to the trace 702.

In an embodiment, the patch antenna 460 includes a feedthrough via 720 electrically connected to the trace 702 between the first end 704 and the second end 706. The feedthrough via 720 can be a metal via that extends from the trace 702 through the dielectric layer 502, e.g., radially inward from the trace.

Figure 8:
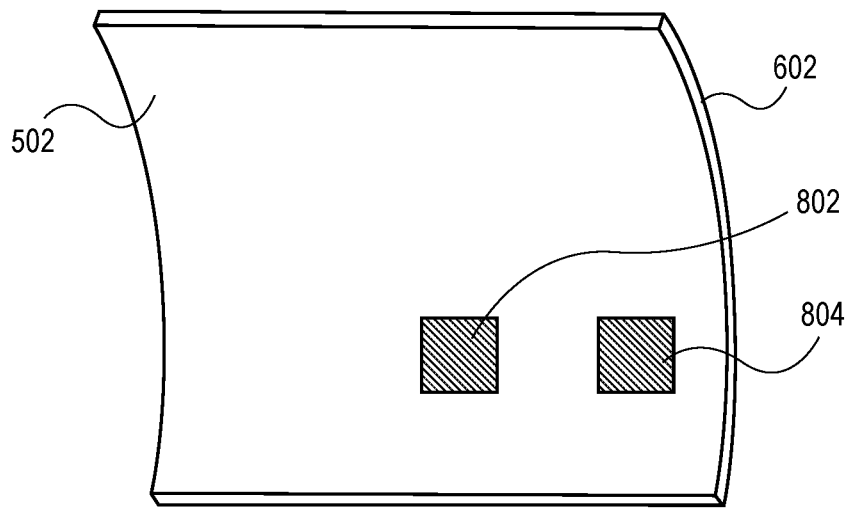
FIG. 8 is a bottom view of a dielectric layer of a patch antenna, in accordance with an embodiment.

Referring to FIG. 8, a bottom view of a dielectric layer of a patch antenna is shown in accordance with an embodiment. The feedthrough via 720 can extend from the trace 702 to a feedthrough contact 802 on the inner surface 602 of the dielectric layer 502. For example, the feedthrough contact 802 can be sputtered platinum and may be interconnected with the trace 702 by the feedthrough via 720 extending vertically through the dielectric layer 502.

Referring again to FIG. 7, the length of the trace 702 may be half of the wavelength of the resonating frequency. Such a length is typical of patch antennas 460 having non-undulating conductor patterns. Non-undulating conductor patterns having such a length, however, may not fit within the circumference of the annular wall 414. The undulating pattern of the trace 702, on the other hand, can allow such a length to fit within the circumference of the biostimulator 100. A longitudinal and circumferential width of the dielectric layer 502 may be varied to accommodate the length of the trace 702. More particularly, varying the area of the dielectric layer 502 can accommodate metal layers 506 of different shapes or sizes. Increased longitudinal width can allow for the longitudinal segments 708 of the trace 702 to increase, and increased circumferential width can allow for more longitudinal segments 708 to be fit around the circumference of the annular wall 414. Thus, an increased trace 702 length may be accommodated by increasing a profile of the dielectric layer 502.

Although different shapes and sizes of metal layers 506 may be accommodated by varying the profile of the dielectric layer 502, in some cases the circumference of the annular wall 414 may be too small to accommodate a trace 702 length having half the wavelength of the resonant frequency. In an embodiment, the length of the trace 702 can be further reduced to a quarter wavelength by shorting one end of the trace 702. More particularly, the patch antenna 460 may include a ground via 722 connected to the trace 702 between the first end 704 and the feedthrough via 720. The ground via 722 can be connected to the annular wall 414 (the ground plane) to form a shorted patch antenna 460. For example, referring again to FIG. 8, the ground via 722 can extend from the trace 702 through the dielectric layer 502 to a ground contact 804 on the inner surface 602 of the dielectric layer 502. The ground contact 804 can include platinum sputtered on the inner surface 602.

Integration of the ground via 722 between the first end 704 and the feedthrough via 720 to form the shorted patch antenna 460 can reduce the required length of the trace 702 to a quarter wavelength of the resonant frequency. More particularly, the patch antenna 460 can have a resonant frequency at a predetermined signal wavelength, and the length of the trace 702 from the feedthrough via 720 to the second end 706 may be one quarter of the predetermined signal wavelength when the ground via 722 is used. One skilled in the art will appreciate that the shorted patch antenna 460 may have a reduced radiation efficiency as compared to a non-shorted patch antenna 460. In the case of an implantable biostimulator 100, however, the need for compactness may outweigh the need for radiation efficiency, and thus, the counterintuitive shorting of the antenna may be justified.

The predetermined signal wavelength corresponds to the resonant frequency of the patch antenna 460. It is contemplated that the patch antenna 460 may be used to communicate wireless signals above 1 GHz. Lower resonant frequencies may require trace lengths that exceed the circumference of the annular wall 414. Thus, the length of the trace 702 may be determined accordingly. For example, the patch antenna 460 may be used for BLE communications, and thus, may have a resonant frequency of 2.4 GHz. The trace length could therefore be a quarter of the concomitant resonant wavelength, e.g., 3.125 cm.

In addition to the trace length, several other factors may affect the resonant frequency of the patch antenna 460. For example, the dielectric spacing between longitudinal segments 708 of the trace 702 can affect the resonant frequency. More particularly, a length of the circumferential segments 710 between the longitudinal segments 708 can affect the capacitance of the patch antenna 460 such that the larger the circumferential spacing, the lower the resonant frequency may be. Furthermore, the distance between the feedthrough via 720 (used to feed a wireless radiofrequency signal to or from the electronic circuitry) and the ground via 722 (used to short the conductor to the ground plane) can affect the resonant frequency. More particularly, the shorter the distance between the feedthrough via 720 and the ground via 722, the lower the resonant frequency may be. Accordingly, several factors may be adjusted to achieve the desired resonant frequency, including the trace length, a distance between the ground via 722 and the feedthrough via 720, and the circumferential spacing between longitudinal segments 708 of the trace 702.

Figure 9:
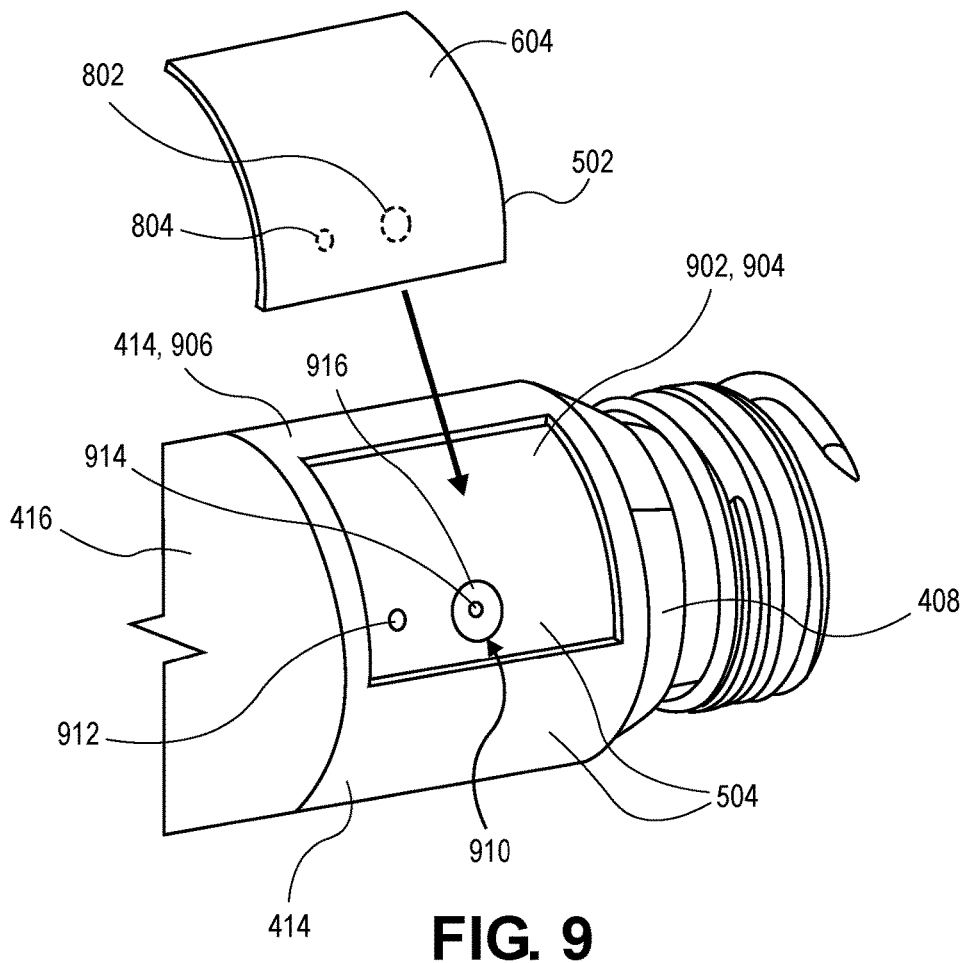
FIG. 9 is an exploded view of a patch antenna integrated into a housing of a biostimulator, in accordance with an embodiment.

Referring to FIG. 9, an exploded view of a patch antenna integrated into a housing of a biostimulator is shown in accordance with an embodiment. The dielectric layer 502 of the patch antenna 460 can fit closely, e.g., conform to, the outer surface 504 of the annular wall 414. For example, the annular wall 414 may include a cavity 902 sized and shaped to receive the dielectric layer 502. The cavity 902 can include a first portion 904 of the outer surface 504 recessed below a second portion 906 of the outer surface 504. The first portion 904 may be recessed in that a radial distance from the longitudinal axis 406 to the first portion 904 of the outer surface 504 may be less than a radial distance from the longitudinal axis 406 to the second portion 906 of the outer surface 504. A profile, e.g., a longitudinal and circumferential width, a perimeter, a surface area, etc., of the cavity 902 can match the profile of the dielectric layer 502. Accordingly, the dielectric layer 502 can be mounted in the cavity 902 such that the dielectric layer 502 fills the cavity 902 and conforms to the outer surface 504.

In an embodiment, electrical contacts, which correspond to the feedthrough contact 802 and the ground contact 804 on the inner surface 602 of the dielectric layer 502, may be located on the outer surface 504 of the annular wall 414. For example, the patch antenna 460 may include an electrical feedthrough 910 passing through the annular wall 414 from the outer surface 504 to the interior surface 508. The electrical feedthrough 910 can include an external contact aligned with the feedthrough contact 802 of the dielectric layer 502 mounted on the annular wall 414.

The electrical feedthrough 910 can include a feedthrough pin 914 that passes through a hole in the annular wall 414. The feedthrough pin 914 can be surrounded by a feedthrough insulator 916, e.g., an annular ceramic sleeve, that separates the feedthrough pin 914 from the annular wall 414. The feedthrough pin 914 can electrically connect to circuitry on in the electronics compartment 412, e.g., through a compression connector or a wire bond. Accordingly, the feedthrough pin 914 can be insulated from the annular wall 414 to carry an electrical signal between an internal radiofrequency circuit of the electronic circuitry on an interior of the annular wall 414 to the external metal layer 506 on the exterior of the annular wall 414 (through the annular wall 414). The electrical feedthrough 910 can hermetically seal the electronics compartment 412 from a surrounding environment, in addition to providing the electrical pass-through functionality.

The patch antenna 460 may include a wall ground contact 912 on the outer surface 504. The wall ground contact 912 can be an external contact aligned with the ground contact 804 of the dielectric layer 502 mounted on the annular wall 414. The wall ground contact 912 may be a sputtered contact of a different material or simply a region of the outer surface 504. Accordingly, when the dielectric layer 502 is mounted in the cavity 902, the feedthrough contact 802 is electrically connected to the electrical feedthrough 910 and the ground contact 804 is electrically connected to the annular wall 414.

The electrical contact between the components can be maintained by joints. For example, the feedthrough contact 802 can be electrically connected to the electrical feedthrough, e.g., the feedthrough pin 914, by a first joint, and the ground contact 804 can be electrically connected to the wall ground contact 912 by a second joint. The joints may include a weld, a brazing joint, a conductive adhesive, or another electrically conductive joint.

Figure 10:
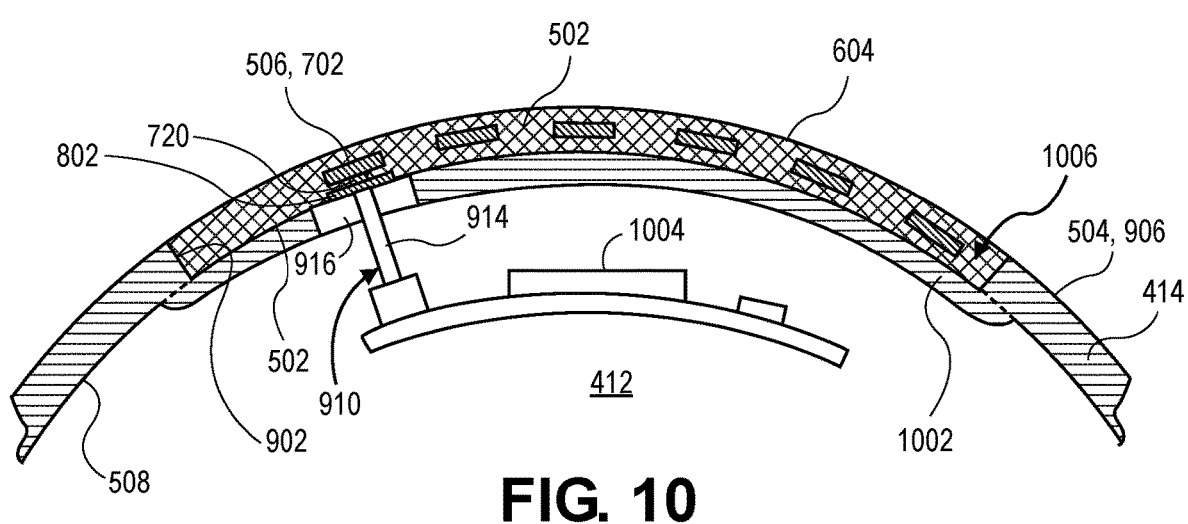
FIG. 10 is a sectional view of a patch antenna, in accordance with an embodiment.

As shown in FIGS. 9 and 10, an outer dimension, e.g., a width or a diameter, of the feedthrough insulator 916 can be larger than an outer dimension, e.g., a width or a diameter, of the feedthrough contact 802. Accordingly, when the patch antenna 460 is mounted in the cavity 902 with the contacts 802, 914 aligned with each other, the larger width of the insulator 916 can ensure that the feedthrough contact 802 does not contact the outer surface 504 of the annular wall 414, which laterally surrounds the insulator 916. More particularly, the insulator 916 can be sized and positioned to electrically isolate the feedthrough contact 802 from the annular wall 414.

The annular wall 414 may be connected to other conductive components of the biostimulator 100. For example, the annular wall 414 may be welded at a proximal end to the energy source container 416 and/or at a distal end to a flange of the header assembly 408. The energy source container 416 and the flange may be metallic, and thus, the connection between the ground contact 804 and the wall ground contact 912 may effectively ground the trace 702 to one or more components of the biostimulator enclosure. Accordingly, the electrical feedthrough 910 can feed radiofrequency signals from the electronic circuitry to the metal layer 506 to cause the trace 702 to radiate with respect to the enclosure of the biostimulator 100, which acts as the ground plane.

Referring to FIG. 10, a sectional view of a patch antenna is shown in accordance with an embodiment. Embedding the metal layer 506 within the dielectric layer 502 can be advantageous. The dielectric layer 502 can provide significant isolation from tissue dielectric variability. Second, the dielectric layer 502 can keep the near-field radiation contained to help reduce the specific absorption rate (SAR) of radiation into the tissue. In short, the dielectric layer 502 acts as the separation between the metallic layers of the patch antenna 460 (the trace 702 and the annular wall 414 of the biostimulator enclosure) and governs the radiation performance of the patch antenna 460.

The dielectric layer 502 governs the radiation performance in part by containing near-field radiation. When the patch antenna operates, a voltage is at a maximum on either side of the dielectric layer 502 and at a minimum at the center of the dielectric layer 502. By contrast, current is at a maximum at the center of the dielectric layer 502 and at a minimum on the edges. Horizontal components of the fringing fields of the radiation at the edges are in phase and add up to cause the patch antenna 460 to radiate. Far-field radiation communicates information to an external device in the surrounding environment. By contrast, near-field radiation is transmitted into and lost within the surrounding tissue, providing no communicative benefit and resulting in lost power. To improve device efficiency, near-field containment can be increased in any of several ways.

In an embodiment, the dielectric layer 502 has a high dielectric constant. For example, the dielectric constant of the dielectric layer 502 may be greater than 8. In an embodiment, the dielectric constant is in a range of 8 to 12, e.g., 10. The dielectric constant may be higher than 12, however. For example, exotic materials may be used to form the dielectric layer 502 having a dielectric constant of 15 to 20, or higher. Such dielectric constants can improve containment of the near-field radiation. When the patch antenna 460 is implanted in variable biological conditions, there is no strict control over the surrounding dielectric constant, and the high dielectric ceramic material helps the patch antenna 460 to be less affected by variation in the biological tissue. This can serve several purposes. First, the resonance frequency and radiation efficiency do not vary substantially with changing biological conditions. Secondly, the input impedance of the patch antenna 460 does not change substantially to cause variable insertion loss. The patch antenna 460 can be tuned to have certain input impedances by changing the feed location. For example, the location at which the feedthrough via 720 connects to the trace 702 may be moved toward the shorted end 704 of the trace 702 to reduce the input impedance. By contrast, the connection between the feedthrough via 720 and the trace 702 may be moved towards the second end 706 to increase the input impedance. The longitudinal and circumferential width of the trace 702 can control a bandwidth of the patch antenna 460. It is noted that the resonance frequency of the patch antenna 460 may also be adjusted by changing a location of the trace short.

In addition, having a high dielectric constant, a thickness of the dielectric layer 502 may be maximized to increase containment of the near-field radiation. It is noted that a thickness of the dielectric layer 502 may be, but is not necessarily, limited by a thickness of the annular wall 414. More particularly, it is contemplated that locating the outer surfaces of the dielectric layer 502 and the annular wall 414 at a same radial location, e.g., making the outer surfaces of those components flush with each other, can help maintain a compact device profile and reduce a likelihood of snags as the biostimulator 100 is delivered or retrieved through the patient anatomy. Accordingly, the dielectric layer 502 may be mounted on the annular wall 414 such that the exterior surface 604 of the dielectric layer 502 is at a same radial distance from the longitudinal axis 406 as the second portion 906 of the outer surface 504. The cavity 902 may extend from the outer surface to a location less than the thickness of the annular wall 414, and the annular wall 414 may be thicker than the dielectric layer 502 to receive the dielectric layer 502 in this configuration.

Alternatively, the dielectric layer 502 may protrude radially above the outer surface of the annular wall 414. The cavity 902 may extend from the outer surface to a depth that is less than the thickness of the dielectric layer 502 and/or the dielectric layer 502 may be thicker than the annular wall 414. In either case, the exterior surface 604 of the dielectric layer 502 may be radially outward from the outer surface 504 of the annular wall 414. In such cases, the lateral edges 606 of the dielectric layer 502 may be chamfered, or a fillet of material, such as adhesive, may be placed around the lateral edges 606, to prevent snags when tracking the biostimulator 100 through the patient anatomy.

The cavity 902 that receives the dielectric layer 502 may be formed in any of several manners. As described above, the cavity 902 an be formed by etching, or the cavity 902 can be formed by machining. In an embodiment, the annular wall 414 may be bent or indented to create the cavity 902 where the dielectric layer 502 is mounted. Indentation of the annular wall 414 could be provided by a stamping process, by way of example. Indenting the annular wall 414 to form an indented wall 1002 can allow the enclosure wall thickness to be preserved. The indentation may have a depth equal to a thickness of the dielectric layer 502, e.g., 0.01 inches. Accordingly, when the dielectric layer 502 is mounted in the cavity 902, the exterior surface 604 of the dielectric layer 502 may be flush with the outer surface 504 of the annular wall 414. In the case of the annular wall 414 and the dielectric layer 502 having equal thicknesses, the inner surface 602 of the dielectric layer 502 may be at a same radial level as the interior surface 508 of the annular wall 414.

The electrical feedthrough 910 can extend from the trace 702 through the dielectric layer 502 and the indented wall 1002 to reach into the electronics compartment 412. Electrical feedthrough 910 may be connected to electronic circuitry 1004, which as described above, can include the wireless communication circuitry used to send or receive signals through the trace 702. Accordingly, the electrical feedthrough 910 can electrically interconnect the feedthrough via 720 in the dielectric layer 502 to the electronic circuitry 1004 in the electronics compartment 412. The electronic circuitry 1004 may also be connected to the electrode 402 through the header assembly 408 to send or receive sensing or pacing impulses to the target tissue 102.

In an embodiment, the electrical feedthrough 910 can be electrically connected to the feedthrough contact 802 by a wire lead. Similarly, the ground contact 804 may be electrically connected to the wall ground contact 912 on the housing 110 by a wire lead. Accordingly, electrical interconnections between the structures described above may be made in various manners in addition to those specifically described above.

It is noted that the distance between the metal layer 506 and the ground plane can adjust the resonance frequency of the patch antenna 460, and thus, the radial distance at which the trace 702 is embedded within the dielectric layer 502 can be varied to tune the resonant frequency.

In an embodiment, a section of the enclosure wall may be removed to fit the dielectric layer 502 into the annular wall 414. For example, the cavity 902 may include a hole 1006 in the annular wall 414. The hole 1006 can extend entirely through the annular wall 414 from the outer surface 504 to the interior surface 508. Although not shown, it will be appreciated that such a hole 1006 could be sized and shaped like the indentation shown in FIG. 10, however, the throughhole 1006 would have no indented wall 1002 separating the cavity 902 from the electronics compartment 412. The hole 1006 can be formed by machining processes, such as drilling, milling, or laser cutting. The dielectric layer 502 can be mounted within the hole 1006. More particularly, the dielectric layer 502 can be inserted into the removed wall section to fill the hole 1006. The dielectric layer 502 can be brazed directly to the annular wall 414 to create a hermetic seal between the electronics compartment 412 and the surrounding environment. In an embodiment, the dielectric layer 502 and the annular wall 414 have a same thickness, e.g., 0.01 inches, such that the inner and outer surfaces of the components are flush with each other at a same radial distance from the longitudinal axis 406.

Referring to FIG. 11, a sectional view of a patch antenna is shown in accordance with an embodiment. The patch antenna 460 can include a trace 702 formed from several stacked trace segments. For example, the trace 702 can be formed by a first metal layer 506A and a second metal layer 506B, which are electrically connected and positioned at different radial distances from the central axis of the device. More particularly, the first metal layer 506A is radially inward from the second metal layer 506B. The metal layers can be electrically connected by a trace via 1102 extending radially outward from a second end 706 of the first metal layer 506A to a first end 704 of the second metal layer 506B. Accordingly, a communication signal delivered to the first metal layer 506A through the feedthrough pin 914 can be transmitted through an entire length of the trace 702 over both the first and second layers. As described above, the overall trace length is determined by the stacked undulating path formed by multiple metal layers 506A to 506n, e.g., to 506B.

The first metal layer 506A of the trace 702 can be a first trace segment or layer and one or more additional trace segments or layers, e.g., the second metal layer 506B, can be stacked on the first trace segment in a radial direction. In an embodiment, the trace segments can be offset in a circumferential direction. For example, the longitudinal segments 708 of the first metal layer 506A can be shifted relative to the longitudinal segments 708 of the second metal layer 506B. This is evident from the longitudinal segments in one layer being circumferentially aligned with gaps between the longitudinal segments in another layer. The circumferential offset may reduce interference of radiated signals from the layers, and thus, may improve signal quality or efficiency.

FIG. 11 illustrates a patch antenna 460 formed by deposition techniques. In an embodiment, the deposition techniques can form the insulating and conductive materials of the patch antenna 460 in respective contiguous structures. First, a hole can be drilled through the annular wall 414, e.g., through the indented wall 1002, to form an opening from the outer surface 504 to the inner surface 508. The insulating material can then be built up within the hole and the cavity in the annular wall 414 using deposition techniques. The insulating material can be formed in one or more layers. For example, the insulating material can be built up in a first layer within the hole in the annular wall 414, a second layer between the annular wall and the metal layer 506, and a third layer over the metal layer 506. The layers can be built up in sequence with one or more deposition operations used to form the conductive material. For example, the conductive material can be built up in a first layer within a hole formed through the first layer of the insulating material to form a via 1104. The first metal layer 506A can be built up in another deposition operation to be connected with the via 1104, and one or more other operations can be used to form the via 1102 and the second metal layer 506B.

In an embodiment, rather than being a portion of the electrical feedthrough 910 (FIG. 10), the feedthrough pin 914 can be a pin or wire that is wire bonded to the via 1104 and the electronic circuitry within the electronics compartment 412. For example, the via 1104 can be a metallic tubular structure that a first end of the feedthrough pin 914 can be inserted into and bonded to. A second end of the feedthrough pin 914 can be bonded to the electronic circuitry.

The deposition techniques can provide hermetic seals between the annular wall 414, the insulating material, and the conductive material, and thus, the patch antenna 460 can prevent ingress of fluids or vapors into the electronic compartment 412. The patch antenna 460 of FIG. 11 can be a monolithic structure, e.g., with the dielectric layer 502 and the metal layer 506 integrated directly with the annular wall 414, rather than being formed from several structures bonded together as described above with respect to FIGS. 9-10.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A patch antenna, comprising:
   a cylindrical wall having a cylindrical outer surface, wherein the cylindrical wall is a ground plane of the patch antenna, wherein the cylindrical wall includes a cavity having a shape of a cylindrical arc section between the cylindrical outer surface and a recess surface, and a recess perimeter wall laterally surrounding the cavity between the recess surface and the cylindrical outer surface;
   a dielectric layer having the shape of the cylindrical arc section and mounted on the recess surface within the cavity such that the recess perimeter wall laterally surrounds a lateral perimeter edge of the dielectric layer, wherein the lateral perimeter edge laterally surrounds an exterior surface of the dielectric layer, and wherein the dielectric layer fills the cavity and the exterior surface of the dielectric layer is flush with the cylindrical outer surface of the cylindrical wall along the recess perimeter wall;
   a metal layer embedded within the dielectric layer, wherein the metal layer is a conductor of the patch antenna and includes a trace having an undulating pattern, wherein the trace extends from a first end through a turnback having a first longitudinal segment interconnected to a second longitudinal segment by a circumferential segment;
   a feedthrough via to feed a signal to the metal layer, wherein the feedthrough via is connected to the first longitudinal segment between the first end and the circumferential segment; and
   a ground via connected to the first longitudinal segment between the first end and the feedthrough via, wherein the ground via electrically connects the first longitudinal segment to the cylindrical wall.

2. The patch antenna of claim 1, wherein the cylindrical outer surface of the cylindrical wall is at least a portion of a circular cylinder extending around a longitudinal axis, and wherein the dielectric layer has an inner surface conforming to the recess surface.

3. The patch antenna of claim 2, wherein the trace extends over a length between the first end and a second end, and wherein the undulating pattern includes a plurality of turnbacks.

4. The patch antenna of claim 3, wherein the feedthrough via extends from the trace through the dielectric layer to a feedthrough contact on the inner surface of the dielectric layer.

5. The patch antenna of claim 4, wherein the ground via extends from the trace through the dielectric layer to a ground contact on the inner surface of the dielectric layer.

6. The patch antenna of claim 5, wherein the patch antenna has a resonant frequency at a predetermined signal wavelength, and wherein the length of the trace from the feedthrough via to the second end is one-quarter of the predetermined signal wavelength.

7. The patch antenna of claim 6 further comprising an electrical feedthrough passing through the cylindrical wall from the cavity, wherein the feedthrough contact is electrically connected to the electrical feedthrough and the ground contact is electrically connected to the cylindrical wall.

8. The patch antenna of claim 7, wherein the recess surface is recessed below the cylindrical outer surface, and wherein the exterior surface of the dielectric layer is at a same radial distance from the longitudinal axis as the cylindrical outer surface.

9. The patch antenna of claim 7, wherein the cavity includes a hole in the cylindrical wall, and wherein the dielectric layer fills the hole.

10. The patch antenna of claim 1, wherein the cylindrical wall is thicker than the dielectric layer.

11. A housing for a biostimulator, comprising:
a cylindrical wall having a cylindrical outer surface, wherein the cylindrical wall is a ground plane of a patch antenna, wherein the cylindrical wall includes a cavity having a shape of a cylindrical arc section between the cylindrical outer surface and a recess surface, and a recess perimeter wall laterally surrounding the cavity between the recess surface and the cylindrical outer surface;
a dielectric layer having the shape of the cylindrical arc section and mounted on the recess surface within the cavity such that the recess perimeter wall laterally surrounds a lateral perimeter edge the dielectric layer, wherein the lateral perimeter edge laterally surrounds an exterior surface of the dielectric layer, and wherein the dielectric layer fills the cavity and the exterior surface of the dielectric layer is flush with the cylindrical outer surface of the cylindrical wall along the recess perimeter wall; and
a metal layer embedded within the dielectric layer, wherein the metal layer is a conductor of the patch antenna and includes a trace having an undulating pattern, wherein the trace extends from a first end through a turnback having a first longitudinal segment interconnected to a second longitudinal segment by a circumferential segment, a feedthrough via to feed a signal to the metal layer, wherein the feedthrough via is connected to the first longitudinal segment between the first end and the circumferential segment, and a ground via connected to the first longitudinal segment between the first end and the feedthrough via, wherein the ground via electrically connects the first longitudinal segment to the cylindrical wall.

12. The housing of claim 11, wherein the cylindrical outer surface of the cylindrical wall is at least a portion of a circular cylinder, and wherein the dielectric layer has an inner surface conforming to the recess surface.

13. The housing of claim 12, wherein the trace extends over a length between the first end and a second end, and wherein the undulating pattern includes a plurality of turnbacks.

14. The housing of claim 13, wherein the feedthrough via extends from the trace through the dielectric layer to a feedthrough contact on the inner surface of the dielectric layer, and wherein the ground via extends from the trace through the dielectric layer to a ground contact on the inner surface of the dielectric layer.

15. The housing of claim 14 further comprising an electrical feedthrough passing through the cylindrical wall from the cavity, wherein the feedthrough contact is electrically connected to the electrical feedthrough and the ground contact is electrically connected to the cylindrical wall.

16. A biostimulator, comprising:
a housing including a cylindrical wall extending around an electronics compartment, wherein the cylindrical wall has a cylindrical outer surface, wherein the cylindrical wall is a ground plane of a patch antenna, wherein the cylindrical wall includes a cavity having a shape of a cylindrical arc section between the cylindrical outer surface and a recess surface, and a recess perimeter wall laterally surrounding the cavity between the recess surface and the cylindrical outer surface, a dielectric layer having the shape of the cylindrical arc section and mounted on the recess surface within the cavity such that the recess perimeter wall laterally surrounds a lateral perimeter edge of the dielectric layer, wherein the lateral perimeter edge laterally surrounds an exterior surface of the dielectric layer, and wherein the dielectric layer fills the cavity and the exterior surface of the dielectric layer is flush with the cylindrical outer surface of the cylindrical wall along the recess perimeter wall, and a metal layer embedded within the dielectric layer, wherein the metal layer is a conductor of the patch antenna and includes a trace having an undulating pattern, wherein the trace extends from a first end through a turnback having a first longitudinal segment interconnected to a second longitudinal segment by a circumferential segment, a feedthrough via to feed a signal to the metal layer, wherein the feedthrough via is connected to the first longitudinal segment between the first end and the circumferential segment, and a ground via connected to the first longitudinal segment between the first end and the feedthrough via, wherein the ground via electrically connects the first longitudinal segment to the cylindrical wall;
a header assembly mounted on the housing, wherein the header assembly includes a fixation element and an electrode; and
electronic circuitry within the electronics compartment, wherein the electronic circuitry is electrically connected to the metal layer and the electrode.

17. The biostimulator of claim 16, wherein the fixation element includes a helix extending helically to a piercing tip.

18. The biostimulator of claim 16, wherein the undulating pattern extends from the first end to a second end and has a plurality of turnbacks.

19. The biostimulator of claim 18 further comprising an electrical feedthrough passing through the cylindrical wall from the cavity.

20. The biostimulator of claim 19, wherein the electrical feedthrough electrically interconnects the feedthrough via on the dielectric layer to the electronic circuitry in the electronics compartment.

* * * * *